(12) United States Patent
Liu et al.

(10) Patent No.: US 8,367,332 B2
(45) Date of Patent: Feb. 5, 2013

(54) DETECTION AND QUANTIFICATION OF ABASIC SITE FORMATION IN VIVO

(75) Inventors: Lili Liu, Macedonia, OH (US);
Yanming Wang, Beachwood, OH (US);
Stanton Gerson, Hunting Valley, OH (US)

(73) Assignee: Case Western Reserve University, Cleveland, OH (US)

( * ) Notice: Subject to any disclaimer, the term of this patent is extended or adjusted under 35 U.S.C. 154(b) by 339 days.

(21) Appl. No.: 12/610,871

(22) Filed: Nov. 2, 2009

(65) Prior Publication Data

US 2010/0111861 A1     May 6, 2010

Related U.S. Application Data

(60) Provisional application No. 61/110,091, filed on Oct. 31, 2008.

(51) Int. Cl.
*C12Q 1/68* (2006.01)
*C07H 21/00* (2006.01)

(52) U.S. Cl. ........................... 435/6.1; 536/22.1

(58) Field of Classification Search .................. 435/6.1; 536/22.1
See application file for complete search history.

(56) References Cited

U.S. PATENT DOCUMENTS

| 4,863,847 | A * | 9/1989 | Talpaert-Borle et al. | 435/6.13 |
| 6,465,448 | B1 * | 10/2002 | Gerson et al. | 514/183 |
| 6,635,677 | B2 * | 10/2003 | Gerson et al. | 514/645 |
| 2004/0018526 | A1 * | 1/2004 | Hirose et al. | 435/6 |
| 2009/0272657 | A1 * | 11/2009 | Bhatia et al. | 205/792 |

FOREIGN PATENT DOCUMENTS

WO    WO2008/066990    *    5/2008

OTHER PUBLICATIONS

Rosa et al. Nucleic Acids Research 19 (20) : 5569 (1001).*
Liu et al., Clinical Cancer Research 5 :2908 (1999).*
Nakamura et al., Cancer Research 58 : 222 (1998).*
Makrigiorgos et al., Int. J. Radial Biol. 74 (1) : 99 (1998).*
Chastain et al., Nonrandom AP site disreibution in highly proliferative cells. FASEB Journal 20E2127 (2006).*
Liuzzi et al., A new approach to the study of the base-excision repair pathway using methoxyamine. J. of Biologivcal Chemistry 260(9) : 5252 (1985).*
Luo et al., Inhibition of the human apurinic/apyrimidinic endonuclease (APE1) repair activity and sensitization of breast cancer cells to DNA alkylating agents with lucanthone. Anticancer Research 24 :2127 (2004).*
Rosa et al. Processing in vitro of an abasic site reacted with methoxyamine: a new assay for the detection of abasic sites formed in vivo. Nucleic Acids Research 19(20) :5569 (1991).*
Yan et al., Combined Treatment with Temozolomide and Methoxyamine: Blocking Apurininc/Pyrimidinic Site Repair Coupled with Targeting Topoisomerase IIα. Clinical Cancer Research 13 : 1532 (2007).*
Atamna et al., A method for detecting abasic sites in living cells: Age-dependent changes in base excision repair. PNAS 97(2) : 686 (2000).*
Kubo et al., A novel sensitive and specific assay for abasic sites, the most commonly produced DNA lesion. Biochemistry 31 : 3703 (1992).*
Kurisu et al., Quantitation of DNA damage by an aldehyde reactive probe (ARP). Nucleic Acids Research Supplement No. 1 :45-46 (2001).*

* cited by examiner

*Primary Examiner* — Ethan C Whisenant
(74) *Attorney, Agent, or Firm* — Tarolli, Sundheim, Covell & Tummino LLP

(57) ABSTRACT

A method of measuring the efficacy of an anticancer agent in generating abasic (AP) sites in DNA of cancer cells of a subject includes administering to the subject an anticancer agent that generates AP sites in at least one cancer cell and an AP endonuclease inhibitor probe. The AP endonuclease inhibitor probe includes a detection moiety for detecting the probe in the subject. The amount of probe bound to cancer cells of the subject is then measured. The amount of probe bound to cancer cells of the subject is indicative of efficacy of the anticancer agent in generating AP sites in cancer cells of the subject.

20 Claims, 9 Drawing Sheets

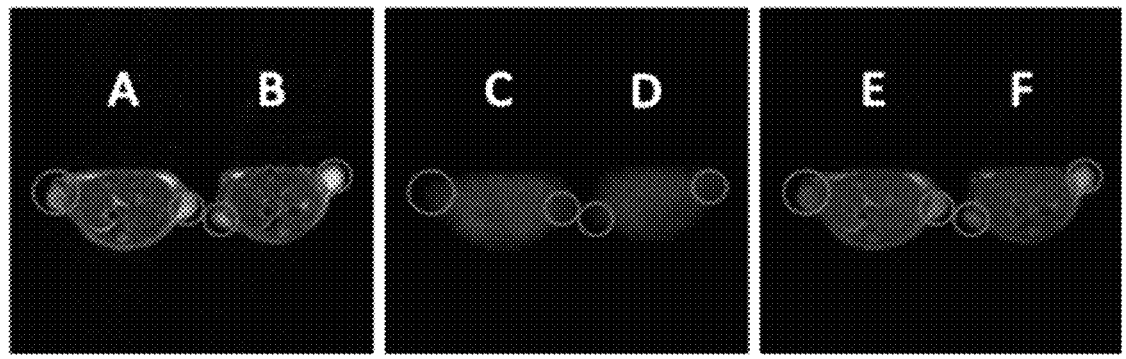
Figs. 1A-F
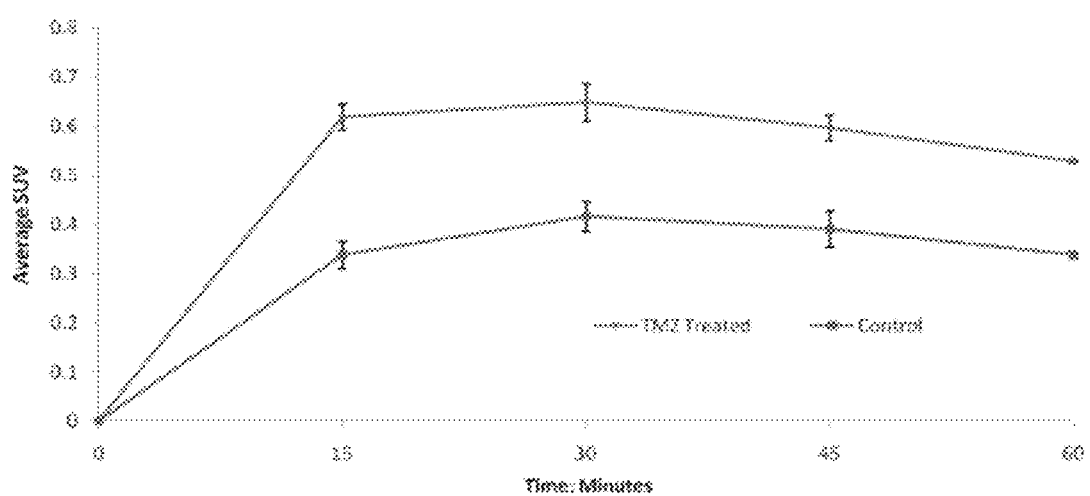
Fig. 2

Figs. 4A-B

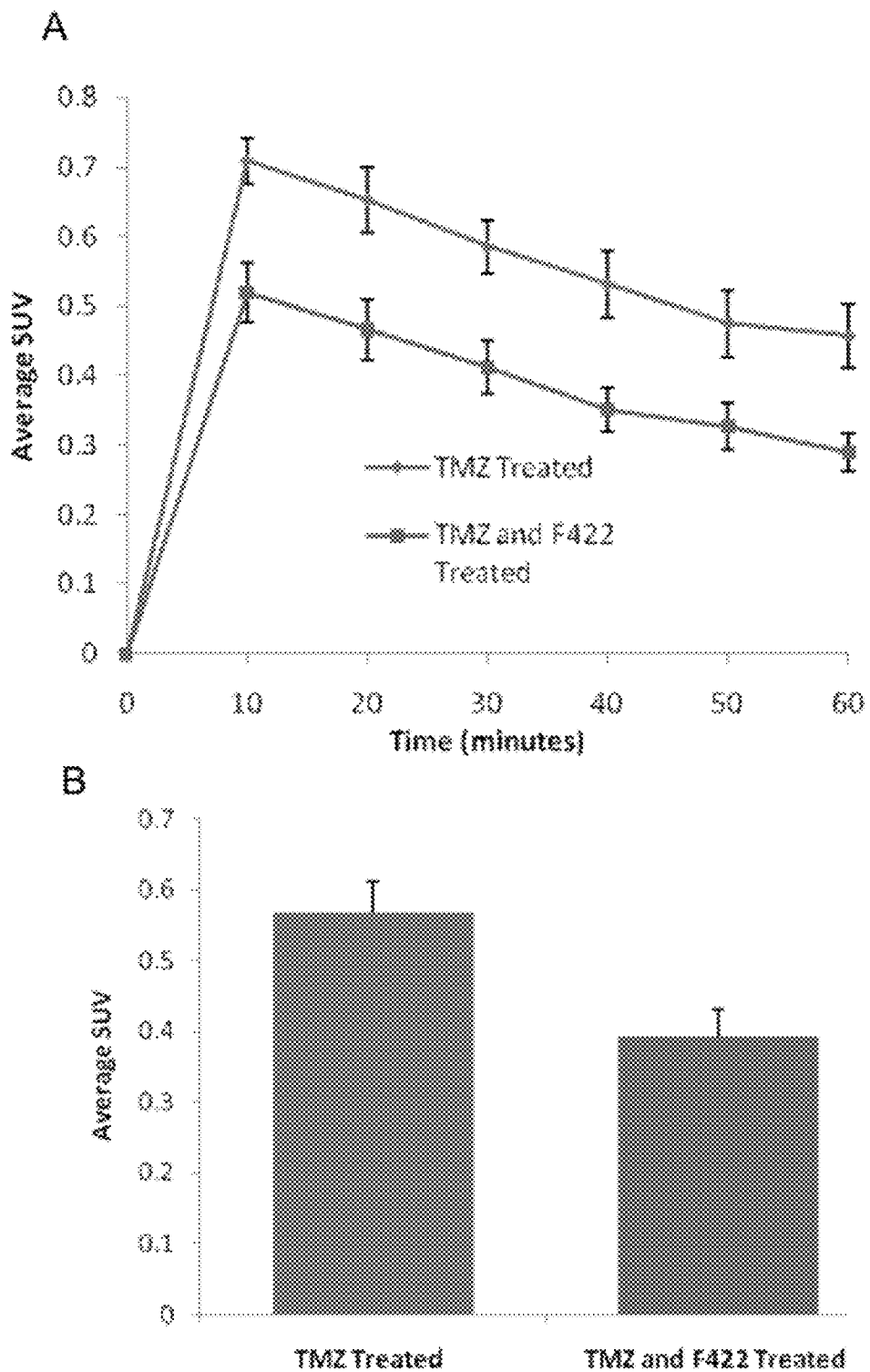
Figs. 6A-B

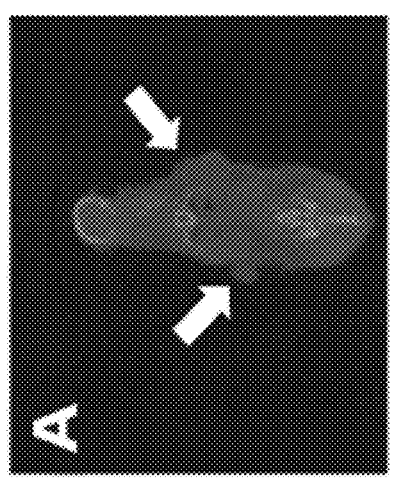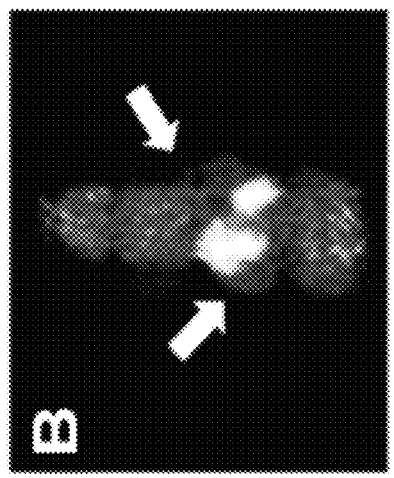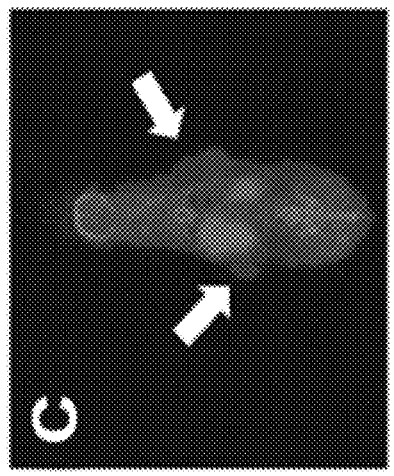
Fig. 7A-C

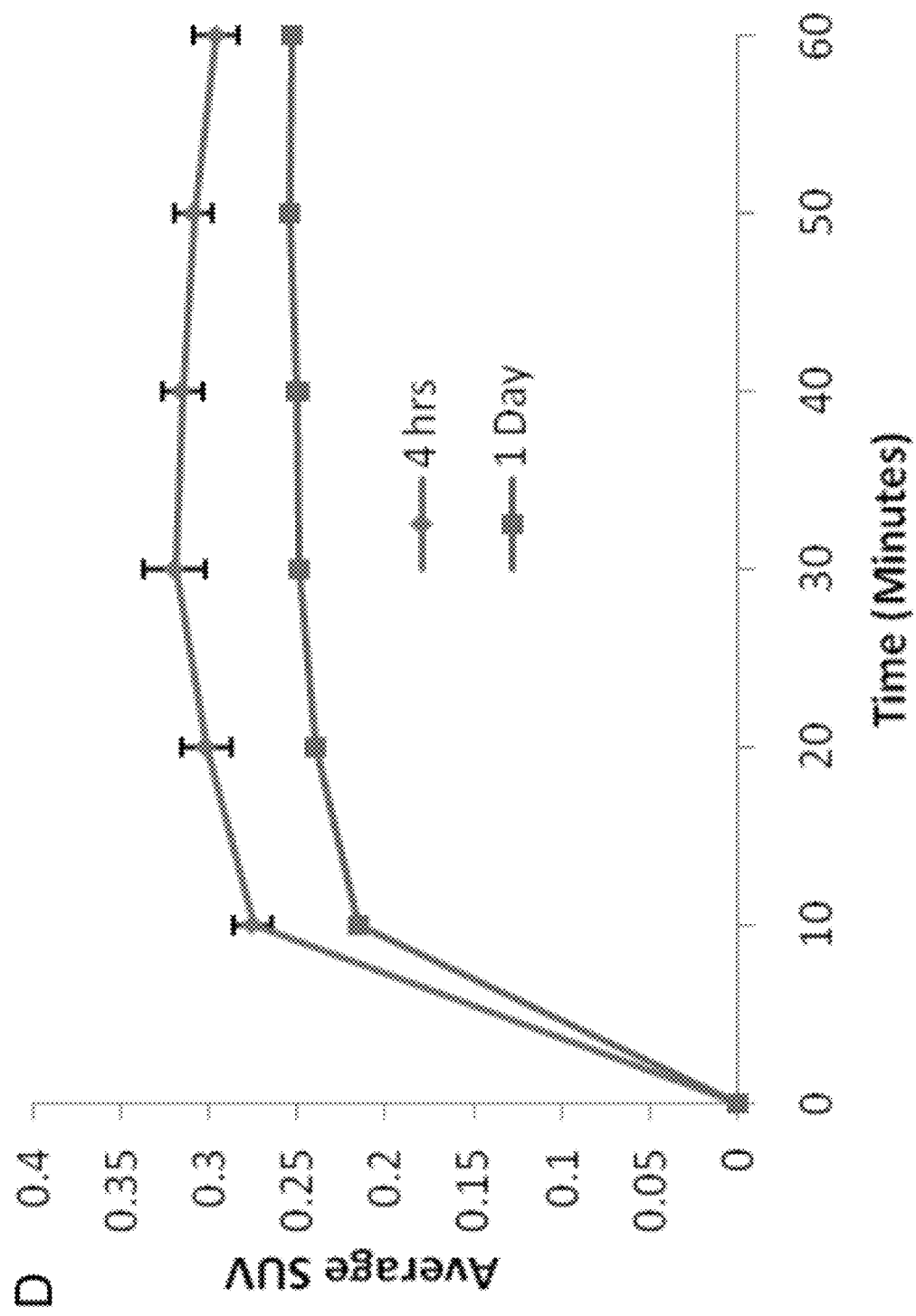

DETECTION AND QUANTIFICATION OF ABASIC SITE FORMATION IN VIVO

RELATED APPLICATION

This application claims priority from U.S. Provisional Application No. 61/110,091, filed Oct. 31, 2008, and U.S. patent application Ser. No. 12/439,626, filed Mar. 2, 2009, the subject matter, which is incorporated herein by reference.

DETAILED DESCRIPTION

The present invention relates to an assay for measurement of genomic DNA apurinic/apyrimidinic (AP) sites in vivo, and more particularly, to a method of detecting and quantifying AP site formation in vivo.

BACKGROUND

Current cancer therapies rely heavily on radiation and DNA damaging agents to induce both cytotoxic DNA changes and programmed cell death (Neidle S, Thurston D E. Chemical approaches to the discovery and development of cancer therapies. Nat Rev Cancer 2005; 5: 285-96). Cytotoxic DNA damages include bulky lesions, inter-strand crosslinks, double-strand breaks, interruption of transcription, replication, and chromosome segregation (Friedberg E C. DNA damage and repair. Nature 2003; 421: 436-40.). These lesions interfere with DNA metabolic processes and inhibit normal cell and tumor growth.

Among the DNA-targeted chemotherapeutic agents is temozolomide (TMZ, 3,4-dihydro-3-methyl-4-oxoimidazo [5,1-d]tetrazine-8-carboxamide), which has been widely utilized in cancer therapies (Stevens M F, Hickman J A, Langdon S P, et al. Antitumor activity and pharmacokinetics in mice of 8-carbamoyl-3-methyl-imidazo[5,1-d]-1,2,3,5-tetrazin-4 (3H)-one (CCRG 81045; M & B 39831), a novel drug with potential as an alternative to dacarbazine. Cancer Res 1987; 47: 5846-52.). The drug easily penetrates the blood-brain barrier making it particularly useful in treating malignant brain tumors (Newlands E S, Stevens M F, Wedge S R, Wheelhouse R T, Brock C. Temozolomide: a review of its discovery, chemical properties, pre-clinical development and clinical trials. Cancer Treat Rev 1997; 23: 35-61.). It has shown promising antitumor activity in recent clinical trials (Taliansky-Aronov A, Bokstein F, Lavon I, Siegal T. Temozolomide treatment for newly diagnosed anaplastic oligodendrogliomas: a clinical efficacy trial. J Neurooncol 2006; 79: 153-7; Trudeau M E, Crump M, Charpentier D, et al. Temozolomide in metastatic breast cancer (MBC): a phase II trial of the National Cancer Institute of Canada-Clinical Trials Group (NCIC-CTG). Ann Oncol 2006; 17: 952-6; Hegi M E, Diserens A C, Godard S, et al. Clinical trial substantiates the predictive value of O-6-methylguanine-DNA methyltransferase promoter methylation in glioblastoma patients treated with temozolomide. Clin Cancer Res 2004; 10: 1871-4; Lanzetta G, Campanella C, Rozzi A, et al. Temozolomide in radio-chemotherapy combined treatment for newly-diagnosed glioblastoma multiforme: phase II clinical trial. Anticancer Res 2003; 23: 5159-64). However, drug resistance remains a critical consequence, often causing treatment failure in clinical use (Mason W P, Cairncross J G. Drug Insight: temozolomide as a treatment for malignant glioma—impact of a recent trial. Nat Clin Pract Neurol 2005; 1: 88-95). A major resistance factor is the presence of elaborate mechanisms of DNA repair (Liu L, Gerson S L. Targeted modulation of MGMT: clinical implications. Clin Cancer Res 2006; 12: 328-31). This resistance is based on the fact that TMZ reacts with DNA forming O6-methylguanine (O6mG), 7-methylguanine (N7mG), and 3-methyladenine (N3mA) DNA adducts that are repaired by three major mechanisms.

The O6mG DNA adduct is a cytotoxic and genotoxic lesion mainly repaired by O6-methylguanine DNA-methyltransferase (MGMT) (Gerson S L. MGMT: its role in cancer aetiology and cancer therapeutics. Nat Rev Cancer 2004; 4: 296-307). Cell death from O6mG adducts is also promoted by mismatch repair (MMR) (Modrich P, Lahue R. Mismatch repair in replication fidelity, genetic recombination, and cancer biology. Annu Rev Biochem 1996; 65: 101-33). Deficiency in MMR is associated with pronounced resistance to TMZ (Caporali S, Falcinelli S, Starace G, et al. DNA damage induced by temozolomide signals to both ATM and ATR: role of the mismatch repair system. Mol Pharmacol 2004; 66: 478-91). Meanwhile, N7mG, the dominant lesion formed by TMZ, and N3mA DNA adducts are removed by the base excision repair (BER) pathway (David S S, Williams S D. Chemistry of Glycosylases and Endonucleases Involved in Base-Excision Repair. Chem. Rev 1998; 98: 1221-62; Fromme J C, Verdine G L. Base excision repair. Adv Protein Chem 2004; 69: 1-41; Barnes D E, Lindahl T. Repair and genetic consequences of endogenous DNA base damage in mammalian cells. Annu Rev Genet 2004; 38: 445-76). Efficient BER minimizes the impact of these lesions in normal and tumor cells.

SUMMARY OF THE INVENTION

The present invention relates to a method of measuring the efficacy of an anticancer agent in generating abasic (AP) sites in DNA of cancer cells of a subject. The method includes administering to the subject an anticancer agent that generates AP sites in at least one cancer cell and an AP endonuclease inhibitor probe. The AP endonuclease inhibitor probe includes a detection moiety for detecting the probe in the subject. The amount of probe bound to cancer cells of the subject is then measured. The amount of probe bound to cancer cells of the subject is indicative of the efficacy of the anticancer agent in generating AP sites in cancer cells of the subject.

In an aspect of the invention, the AP endonuclease inhibitor probe can react with an aldehyde of the AP site preventing AP endonuclease cleavage of phosphodiester bonds of the AP site. The AP endonuclease inhibitor probe can also react with an aldehyde of the AP site at a rate faster than AP endonuclease cleaves phosphodiester bonds of the AP site.

In another aspect of the invention, the AP endonuclease inhibitor probe can include at least one of an amine, an aminoxy, a hydrazone, a hydrazine, or a hydroxylamine. The detection moiety can include a radiolabel. In one example, the AP endonuclease inhibitor probe can include methoxyamine in which the carbon of the methyl group is substituted with $^{11}C$, at least one hydrogen of the methyl group is substituted with $^{18}F$, the nitrogen is substituted with $^{13}N$, or the oxygen is substituted with $^{15}O$.

In a further aspect of the invention, the AP endonuclease inhibitor probe can be detected by at least one imaging modality selected from the group consisting of gamma imaging, positron emission tomography (PET) imaging, computer tomography (CT) imaging, magnetic resonance imaging, near infrared imaging, or fluorescent imaging. The anticancer agent can include at least one of an intercalating agent, radiation, a DNA oxidizing agent, an alkylating agent, a radiosensitizing agent, or a cross-linking agent.

The present invention also relates to a method of detecting AP site formation in cancer cells of a subject. The method includes administering to the subject an anticancer agent that generates AP sites in at least one cancer cell and an AP endonuclease inhibitor probe. The AP endonuclease inhibitor probe can include a detection moiety for detecting the probe in the subject. The amount of probe bound to cancer cells of the subject can then be measured. The amount of probe bound to cancer cells of the subject is indicative of the amount of AP sites generated in the cancer cells of the subject by the anticancer agent.

The present invention further relates to a method of quantifying AP site formation in cancer cells of a subject. The method includes administering to the subject an anticancer agent that generates AP sites in at least one cancer cell and an AP endonuclease inhibitor probe. The AP endonuclease inhibitor probe includes a detection moiety for detecting the probe in the subject. The amount of probe bound to cancer cells of the subject is measured by imaging the subject. The amount of probe bound to cancer cells of the subject is indicative of the number of AP sites generated in cancer cells of the subject by the anticancer agent.

BRIEF DESCRIPTION OF THE DRAWINGS

FIG. 1 illustrates an axial view of MRI images of melanoma xenografts acquired by 7T MRI and microPET using [$^{11}$C]MX. [$^{11}$C]MX was injected intravenously (i.v.) (2 mCi/kg) to mice anaesthetized with 1.5-2.0% isoflurane and a 60 min PET scan was performed using a Concord microPET scanner. (A-B) show MRI images of non-treated mouse (A) and the TMZ treated mouse (B). MicroPET images (C-D) were superimposed onto the corresponding slices of the MRI scans (E-F). PET images shown correspond to the activity between 80-110 min. The tumor regions are shown in the circles.

FIG. 2 illustrates a plot showing the radioactivity concentration as a function of time obtained in TMZ-treated tumor regions and non-treated tumor regions as determined in melanoma xenografts. [$^{11}$C]MX (2 mCi/kg) was injected i.v. to mice anaesthetized with 1.5-2.0% isoflurane and a 60 min PET scan was performed. Note that retention of [$^{11}$C]MX in TMZ-treated melanoma tumor regions was higher than in the non-treated tumor regions during the 60-min scan. The radioactivity concentration is expressed in average (n=4, where n is the number of tumors imaged and analyzed) in standard uptake volume [($\mu$ci/cc)/($\mu$ci/g)] (SUV) (decay corrected).

FIG. 6 illustrates left: (A) a plot showing time-radioactivity courses of [$^{11}$C]MX in the melanoma tumors before and after blocking by F422 compound; and (B) average SUV between 0-60 min (n=2 tumors). Decrease of radioactivity concentration indicates in vivo blocking of AP binding sites by F422 compound (p value=0.001).

DETAILED DESCRIPTION

Figure 3:
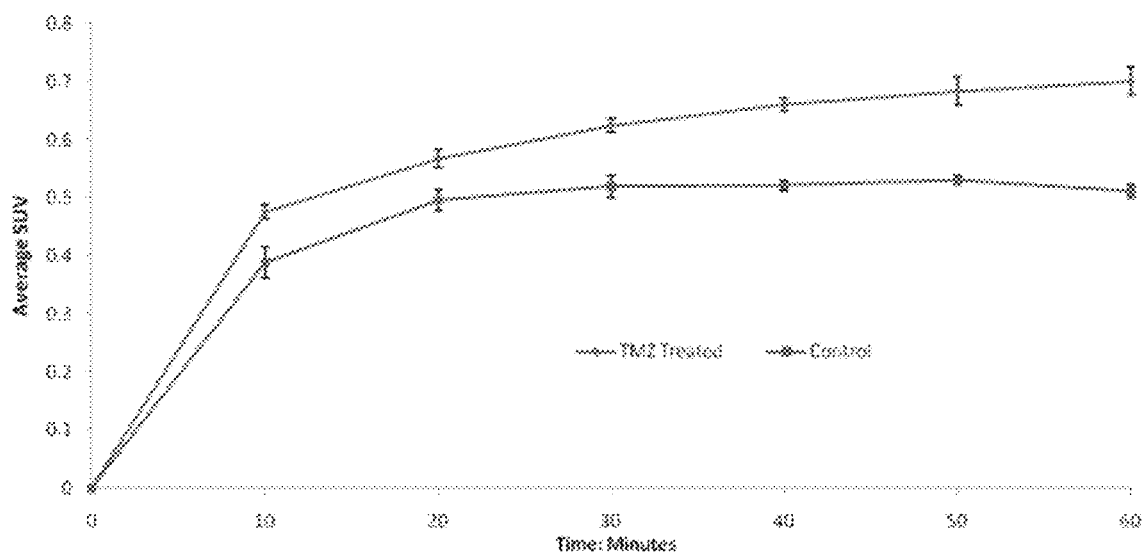
FIG. 3 illustrates a plot showing radioactivity concentrations as a function of time in TMZ-treated tumor regions and non-treated tumor regions as determined in flank glioma xenografts. [$^{11}$C]MX (2 mCi/kg) was injected i.v. to mice anaesthetized with 1.5-2.0% isoflurane and a 60 min PET scan was performed. Similarly, retention of [$^{11}$C]MX in TMZ-treated glioma xenograft tumor regions was higher than in the non-treated tumor regions during the 60-min scan. The radioactivity concentration is expressed in average (n=4, where n is the number of tumors images and analyzed) in standard uptake volume [($\mu$ci/cc)/($\mu$ci/g)] (SUV) (decay corrected).

Methods involving conventional molecular biology techniques are described herein. Such techniques are generally known in the art and are described in detail in methodology treatises, such as Current Protocols in Molecular Biology, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the present invention pertains. Commonly understood definitions of molecular biology terms can be found in, for example, Rieger et al., Glossary of Genetics: Classical and Molecular, 5th Edition, Springer-Verlag: New York, 1991, and Lewin, Genes V, Oxford University Press: New York, 1994.

The terms "patient", "subject", "mammalian host," and the like are used interchangeably herein, and refer to mammals, including human and veterinary subjects.

The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, agent or other material other than directly into a specific tissue, organ, or region of the subject being treated (e.g., brain), such that it enters the animal's system and, thus, is subject to metabolism and other like processes, for example, subcutaneous administration.

The term "cancer", "cancer cell", "tumor", "tumor-cell", "neoplasm", and "neoplastic" cell are used interchangeably and are used herein to mean an abnormal mass of tissue or abnormal proliferation of cells that are uncoordinated with normal tissue or cells surrounding the abnormal tissue or cells.

The present invention relates to an abasic (apurinic/apyrimidinic) (AP) site endonuclease inhibitor probe (i.e., AP endonuclease inhibitor probe) and to the use of the AP endonuclease inhibitor probe in direct imaging and quantifying the generation of AP sites in a subject by administration of an anticancer agent to the subject. Direct imaging and quantitative assessment of AP sites in vivo can be used for efficacy evaluation of DNA-targeted chemotherapies and/or anticancer agents that produce AP sites and invoke base excision repair (BER). Understanding the dynamic of AP site formation and repair can allow clinicians and researchers to determine optimal dose strategies of single and combination chemotherapeutic treatment schedules. Furthermore, with the advent of agents to block BER, direct imaging of AP sites in vivo can be used to determine the optimal dose schedule to potentiate drug administration based on persistence of AP sites. For instance, if one agent induces AP sites, and another blocks BER repair, while a third induces Topo II, understanding the relationship between these events can impact therapeutic efficacy. In addition, direct imaging of AP sites in vivo can facilitate screening of new agents that are designed to either induce AP sites in tumor or cancer cells or block AP sites from DNA repair.

The AP endonuclease inhibitor probe in accordance with one aspect of the present invention can include an amine compound and a detection moiety that can be readily detected in a subject by, for example, imaging, upon administration of the AP endonuclease inhibitor probe to the subject. The AP endonuclease inhibitor when administered to the subject can readily cross the cancer cell membrane, enter the nucleus of the cancer cell, and react with an aldehyde of an AP site generated by an anticancer agent to prevent AP endonuclease cleavage of phosphodiester bonds of the AP site. The AP endonuclease inhibitor probe can also react with an aldehyde of the AP site at a rate faster than the AP endonuclease can cleave phosphodiester bonds of the AP site.

In an aspect of the invention, the AP endonuclease inhibitor probe can include at least one of an amine, an amineoxy, a hydrazone, a hydrazine, or a hydroxylamine that when administered to the subject can readily cross the cancer cell membrane, enter the nucleus of the cancer cell, and react with an aldehyde of an AP site generated by an anticancer agent to prevent AP endonuclease cleavage of phosphodiester bonds of the AP site.

One example of an amine compound in accordance with the present invention is methoxyamine (MX). Other examples of amine compounds in accordance with the present invention can have structures of formula I:

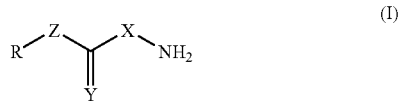

(I)

wherein
X is O or NH;
Y is O, S, or NH;
Z is absent or represents O, S, or NH; and
R represents a hydrogen or a hydrocarbon moiety;
and pharmaceutically acceptable salts thereof.

Other examples of amine compounds that can possess AP endonuclease inhibitory activity (e.g., by binding to AP sites and preventing APE-mediated cleavage of phosphodiester bonds) include other potential inhibitors include O-benzylohydroxylamine; ethyl aminooxyacetate; aminooxyacetic acid; ethyl aminooxyacetate; $H_2NOCHMeCO_2H$; carboxymethoxyamine; aminooxyacetic acid; $HN=C(NH_2)SCH_2CH_2ONH_2$; $H_2NO(CH_2)_3SC(NH_2)=NH$; $MeOC(O)CH(NH_2)CH_2ONH_2$; $H_2NOCH_2CH(NH_2)CO_2H$; canaline; $H_2NO(CH_2)_4ONH_2$; O-(p-nitrobenzyl)hydroxylamine; 2-amino-4-(aminooxymethyl)thiazole; 4-(aminooxymethyl)thiazole; O,O'-(O-phenylenedimethylene)dihydroxylamine; 2,4-dinitrophenoxyamine; O,O'-(mphenylenedimethylene)dihydroxylamine; O,O'-(pphenylenedimethylene)dihydroxylamine; $H_2C=CHCH_2ONH_2$; $H_2NO(CH_2)_4ONH_2$; $H_3C(CH_2)_{15}$—O—NH2, 2,2'-(1,2-ethanediyl)bis(3-aminooxy-)butenedioic acid dimethyl diethyl ester and pharmaceutically acceptable salts of any of these compounds. Other amine compounds that can be used for the AP endonuclease inhibitor probe include AP endonuclease inhibitors disclosed, for example, in U.S. Patent Application Publication No. 2006/0241186.

The detection moiety can include any agent or molecule that can be coupled to, complexed with, and/or is part of the amine compound and that can be readily detected within the subject upon administration to the subject. Examples of detection moieties that can be used in accordance with the present invention include, but are not limited to: various ligands, radionuclides, fluorescent dyes, chemiluminescent agents, microparticles (such as, quantum dots, nanocrystals, phosphors and the like), enzymes (such as, those used in an ELISA, e.g., horseradish peroxidase, beta-galactosidase, luciferase, alkaline phosphatase), colorimetric labels, magnetic labels, and biotin, dioxigenin or other haptens and proteins for which antisera or monoclonal antibodies are available as long as such moieties do not substantially impair the ability of the AP endonuclease probe to readily cross the cancer cell membrane, enter the nucleus of the cell, and bind to AP sites, for example, preferentially compared to AP endonuclease.

In some aspects of the invention, the detection moieties and AP endonuclease inhibitor probes described herein may be used in conjunction with non-invasive imaging (e.g., neuroimaging) techniques for in vivo imaging of the molecular probe, such as magnetic resonance spectroscopy (MRS) or imaging (MRI), or gamma imaging, such as positron emission tomography (PET) or single-photon emission computed tomography (SPECT). The term "in vivo imaging" refers to any method, which permits the detection of a labeled molecular probe, as described above. For gamma imaging, the radiation emitted from the organ or area being examined is measured and expressed either as total binding or as a ratio in which total binding in one tissue is normalized to (for example, divided by) the total binding in another tissue of the same subject during the same in vivo imaging procedure. Total binding in vivo is defined as the entire signal detected in a tissue by an in vivo imaging technique without the need for correction by a second injection of an identical quantity of molecular probe along with a large excess of unlabeled, but otherwise chemically identical compound.

For purposes of in vivo imaging, the type of detection instrument available is a major factor in selecting a given detection moiety. For instance, the type of instrument used will guide the selection of the stable isotope. The half-life should be long enough so that it is still detectable at the time of maximum uptake by the target, but short enough so that the host does not sustain deleterious effects.

In one example, the detection moiety can include a radiolabel that is detected using gamma imaging wherein emitted gamma irradiation of the appropriate wavelength is detected. Methods of gamma imaging include, but are not limited to, SPECT, PET, microPET. For SPECT detection, the chosen radiolabel can lack a particular emission, but will produce a large number of photons in, for example, a 140-200 keV range. For PET detection, the radiolabel can be a positron-emitting moiety, such as $^{11}$C, $^{18}$F, $^{13}$N, and $^{15}$O. The radiolabel can be coupled to, complexed with, and/or substituted for, respectively, carbon, hydrogen, nitrogen, or oxygen of the amine compound.

In one aspect of the invention, the AP endonuclease inhibitor probe can include methoxyamine in which the carbon of the methyl group is substituted with $^{11}$C, at least one hydrogen of the methyl group is substituted with $^{18}$F, the nitrogen is substituted with $^{13}$N, or the oxygen is substituted with $^{15}$O. In one example, the AP endonuclease inhibitor can comprise methoxyamine in which the carbon of the methyl group is substituted with $^{11}$C (i.e., ($^{11}$C)methoxyamine. In another example, the AP endonuclease inhibitor probe can be mono-fluoro, di-fluoro, or tri-fluoro substituted methoxyamine in which at least one fluoro group is substituted with $^{18}$F.

The detection moiety can also include radiolabels, such as $^{75}$B, or $^{76}$Br for PET by techniques well known in the art and are described by Fowler, J. and Wolf, A. in POSITRON EMISSION TOMOGRAPHY AND AUTORADIOGRAPHY (Phelps, M., Mazziota, J., and Schelbert, H. eds.) 391-450 (Raven Press, NY 1986) the contents of which are hereby incorporated by reference. The detection moiety can also include $^{123}$I for SPECT. The $^{123}$I can be coupled to the targeting agent can by any of several techniques known to the art. See, e.g., Kulkarni, Int. J. Rad. Appl. & Inst. (Part B) 18: 647 (1991), the contents of which are hereby incorporated by reference. In addition, detection moiety can include any radioactive iodine isotope, such as, but not limited to $^{131}$I, $^{125}$I, or $^{123}$I. The radioactive iodine isotopes can be coupled to the targeting agent by iodination of a diazotized amino derivative directly via a diazonium iodide, see Greenbaum, F. Am. J. Pharm. 108: 17 (1936), or by conversion of the unstable diazotized amine to the stable triazene, or by conversion of a non-radioactive halogenated precursor to a stable tri-alkyl tin derivative which then can be converted to the iodo compound by several methods well known to the art.

In another example, the detection moiety can an include MRS/MRI radiolabel, such as gadolinium, that is coupled (e.g., attached or complexed) with the amine compound using general organic chemistry techniques.

The detectable moiety can further include known metal radiolabels, such as Technetium-99m (99mTc). Modification of the amine compound agent to introduce ligands that bind such metal ions can be effected without undue experimentation by one of ordinary skill in the radiolabeling art. The metal radiolabeled molecular probes can then be used to detect the formation of AP sited in cancers, such as glioblastomas GBM in the subject. Preparing radiolabeled derivatives of Tc99m is well known in the art. See, for example, Zhuang et al., "Neutral and stereospecific Tc-99m complexes: [99mTc]N-benzyl-3,4-di-(N-2-mercaptoethyl)-amino-pyrrolidines (P-BAT)" Nuclear Medicine & Biology 26(2):217-24, (1999); Oya et al., "Small and neutral Tc(v)O BAT, bisaminoethanethiol (N2S2) complexes for developing new brain imaging agents" Nuclear Medicine & Biology 25(2):135-40, (1998); and Hom et al., "Technetium-99m-labeled receptor-specific small-molecule radiopharmaceuticals: recent developments and encouraging results" Nuclear Medicine & Biology 24(6):485-98, (1997).

The AP endonuclease inhibitor probes can be administered to the subject by, for example, systemic, topical, and/or parenteral methods of administration. These methods include, e.g., injection, infusion, deposition, implantation, or topical administration, or any other method of administration where access to the tissue by the AP endonuclease inhibitor probe is desired. In one example, administration of the AP endonuclease inhibitor probe can be by intravenous injection of the probe in the subject. Single or multiple administrations of the probe can be given. "Administered", as used herein, means provision or delivery of an AP endonuclease inhibitor probe in an amount(s) and for a period of time(s) effective to label cancer cells in the subject. In one example, the AP endonuclease inhibitor probe can be administered by intravenous injection.

AP endonuclease inhibitor probes of the present invention can be administered to a subject in a detectable quantity of a pharmaceutical composition containing a molecular probe or a pharmaceutically acceptable water-soluble salt thereof, to a patient. A "detectable quantity" means that the amount of the detectable compound that is administered is sufficient to enable detection of binding of the compound to the cancer cells. An "imaging effective quantity" means that the amount of the detectable compound that is administered is sufficient to enable imaging of binding of the AP endonuclease inhibitor probes to AP sites of the cancer cells.

In an aspect of the invention, the AP endonuclease inhibitor probe can be used to measure the efficacy of an anticancer agent in generating AP sites in cancers cells of a subject to which the anticancer agent is administered. Measuring the ability of the anticancer agent to generate AP sites in the cancer cells can be used to determine whether a specific anticancer is effective in treating a subject or a specific cancer. If an anticancer agent administered to a subject is found to not generate AP sites, a therapy using an anticancer agent can be halted and another or different anticancer agent can be selected and be administered to the subject. Additionally, the amount or quantity of AP sites generated by an anticancer agent in a subject to which the anticancer agent is administered can be measure and quantified using the AP endonuclease inhibitor probe to determine the efficacy of the therapy. For example, the AP endonucleases inhibitor probe can be used to measure quantity of AP sites generated by an anticancer agent. The greater the number or amount of AP sites generated in cancer cells of the subject measured using the AP endonuclease inhibitor probe the more effective the anticancer agent can be at treating the cancer in the subject.

One example of an anticancer agent that can be administered to a subject and induce the formation of AP sites in cancer cells of a subject is an intercalating agent, such as bleomycin, adriamycin, quinacrine, echinomycin (a quinoxaline antibiotic), and anthrapyrazoles.

Another example of an anticancer agent that can induce the formation of AP sites in cancer cells of a subject is radiation. Radiation, such as gamma radiation, UVA, and UVB, can also be used to generate AP sites according to the methods of the invention. Ultraviolet light is absorbed in DNA with the formation of UV-specific di-pyrimidine photoproducts. Exposure to gamma irradiation, UVA, and UVB can induce damaged pyrimidine photodimers Anticancer agents that induce the formation of AP sites can further include DNA oxidizing agents, such as hydrogen peroxide.

Anticancer agents that induce the formation of AP sites can also include alkylating agents, such as temozolomide (TMZ), 1,3-bis(2-chloroethyl)-I-nitrosourea (BCNU), MeOSO$_2$(CH$_2$)$_2$-lexitropsin (Me-Lex), cis-diamminedichlo-roplatinum II (cisplat; cis-DDP), mitomycin bioreductive alkylating agents, quinones, streptozotocin, cyclophosphamide, nitrogen mustard family members such as chloroambucil, pentostatin (and related purine analogs), fludarabine, bendamustine hydrochloride, chloroethylating nitrosoureas (e.g., lomustine, fotemustine, cystemustine), dacarbazine (DTIC), and procarbazine. In certain embodiments, the alkylating agent is a nitrosoruea, such as a mustine, i.e., a compound having a structure of Formula II, wherein R is an optionally substituted hydrocarbon substituent, such as an alkyl, cycloalkyl, heterocyclyl, aryl, heteroaryl, cycloalkylalkyl, heterocyclylalkyl, aralkyl, or a heteroaralkyl:

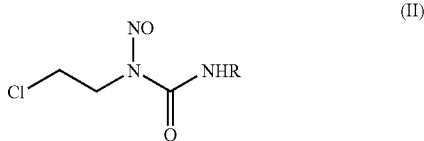

(II)

In some embodiments, the chemotherapeutic is carmustine, BCNU, chlorozotocin, fotemustine, lomustine, nimustine, ranimustine, or semustine. In certain related embodiments, the chloroethyl group of Formula II is replaced by a methyl group, as in streptozocin.

Alkylating agents can function by adding methyl groups to DNA, cross-linking macromolecules essential for cell division, and linking guanine bases in DNA through their N7 atoms. Both inter- and intra-strand cross-links can be mediated by alkylating agents. Inter-strand cross-links prevent the separation of the DNA strands necessary for cell division, and by being more difficult to repair, constitute the more lethal lesion.

In certain embodiments, the anticancer agent is selected from radiosensitizers, such as 5-iodo-2'-deoxyuridine (IUdR), 5-fluorouracil (5-FU), 6-thioguanine, hypoxanthine, uracil, fludarabine, ecteinascidin-743, and camptothecin and analogs thereof.

It will be appreciated that throughout the specification, any recitation of a particular compound should be understood to encompass that compound and any (other) pharmaceutically acceptable salts thereof.

In one aspect of the invention, the method of monitoring the efficacy of an anticancer agent in generating AP sites in cancer cells of a subject in vivo can include the steps of administering in vivo to the subject an anticancer agent at an amount effective to generate AP sites in cancer cells of the subject. The AP endonuclease inhibitor probe can be administered to the subject before, concurrently with the administration of the anticancer agent, and/or after administration of the anticancer agent. The amount or number of AP endonuclease inhibitor probes bound to the AP sites of the cancer cells of the subject can be measured to determine the formation number or amount of AP sites generated or induced by the anticancer agent. In an aspect of the invention, the amount of AP endonuclease inhibitor probes bound to the AP sites of cancer cells of the subject can be measured by visualizing a distribution of the AP endoncuclease inhibitor probes in the subject (e.g., with an in vivo imaging modality as described herein), and then correlating the distribution of the molecular probe with the efficacy of the anticancer agent in generating AP sites.

The number or amount of AP endonuclease inhibitor probes bound to AP sites in cancer cells of the subject can be correlated with the amount of AP sites generated by the anticancer agent by comparing the number or amount of bound AP endonuclease inhibitor probes to a predetermined value. The predetermined value can be based, for example, upon the number or amount of AP endonuclease inhibitor probes bound to cancer cell lines after administration of the AP endonuclease inhibitor probe but prior to administration of the anticancer agent. An increase or substantial increase in the number of bound AP endonucleas inhibitor probes to AP sites of the cancer cells of the subject following administration of the anticancer agent is indicative of the anticancer agent being effective to generate AP sites in the cancer cells of the subject. Conversely, where the number of AP endonuclease inhibitor probes bound to AP sites of the cancer cells is substantially the same or only moderately increased following administration of the anticancer agent, the anticancer is not effective or only moderately effective in generating AP sites in cancer cells of the subject.

In certain embodiments of the invention, the methods and AP endonuclease inhibitor probes of the present invention can be used in an intra-operative surgical procedure, such as a surgical tumor resection, to more readily define and/or image the cancer cell mass or volume during the surgery. In this aspect of the invention, the anticancer agent can be administered to the subject to generate AP sites in cancer cells and the AP endonuclease inhibitor probe can be administered systemically or topically for in vivo imaging of the cancer cells during surgical procedures.

The following examples are included to demonstrate preferred embodiments of the invention. It should be appreciated by those of skill in the art that the techniques disclosed in the examples, which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE

The following example illustrates that MX can be used as a radiotracer for PET imaging of AP sites in vivo. We developed a synthetic approach to [$^{11}$C]MX. Small animal PET (microPET) were then used to evaluate in vivo pharmacokinetic profiles of [$^{11}$C]MX in xenograft tumor mouse models. Because the same imaging modality can be used in clinical setting, the results obtained from microPET can be directly translated into clinical trials.

Radiosynthesis of [$^{11}$C]MX

The radiosynthesis of [$^{11}$C]MX was achieved in two steps as shown in the reaction scheme below.

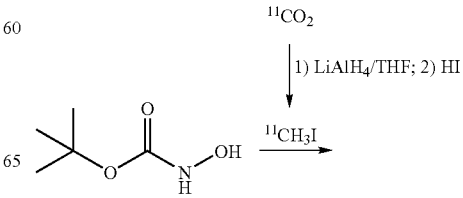

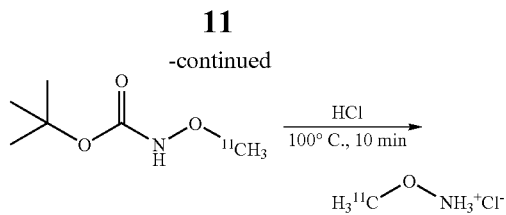

Using an on-site cyclotron, [$^{11}$C]CO$_2$ was first generated, which was reduced to [$^{11}$C]methyl iodide by lithium aluminum hydride. The N-Boc-protected hydroxylamine was then methylated with [$^{11}$C]methyl iodide to yield N-Boc-protected [$^{11}$C]-labeled MX. Following radiomethylation, the Boc-group was then cleaved by hydrochloric acid. The reaction mixture was then neutralized with sodium hydroxide and the product was purified by solid phase extraction using Sep-Pak. HPLC analysis on a cation exchange column indicated that the retention time of the radiolabeled [$^{11}$C]MX as determined by radiodetector was identical to the retention time of the non-labeled MX as determined by UV detection under the same condition. The resulting compound [$^{11}$C]MX is identical to MX except that it incorporates a $^{11}$C instead of a $^{12}$C in the same position. Following radiosynthesis, we conducted MRI and microPET studies in xenograft tumor models to quantitatively determine the in vivo pharmacokinetic profile of [$^{11}$C]MX.

Preparation of Melanoma and Glioma Xenographs

Melanoma and glioma xenografts were prepared according to previously published procedures. Briefly, glioma (U87) and melanoma (WM164) tumor cells (5×10$^6$) were injected into the bilateral flanks of female athymic NRC nude mice (6-8 weeks of age). When the volume of tumor nodules reached 150-200 mm$^3$, mice are randomly assigned to control or treatment groups (4 mice/group).

MRI or CT Studies for Localization of Tumor Regions in the Animal Models

High-resolution MRI studies provide precise location of tumor tissues. For each imaging session, a pair of mice were used and placed on the same holder following anesthesia with 2.0% isoflurane delivered in oxygen gas with a nosecone. After initial localization scans, the two mice were simultaneously scanned with a T2-weighted turbo spin echo acquisition (TR/TE=3000/60 ms, resolution=1 mm×200 um×200 um). Each animal's respiration rate was monitored and adjusted to 50-60 breaths/min by adjusting the isoflurane level. The animal's core body temperature was also maintained at 37±2° C. throughout the scanning procedure by providing a warm air supply to the magnet core. MR images were acquired on a Bruker BioSpec horizontal magnet (7.0T; 30 cm bore) using a transmit/receive mouse volume coil. High-resolution anatomic MR images of the tumor region were acquired using contiguous multi-slice 2D spin echo and 3D gradient echo techniques.

Similarly, an ultra-high resolution micro-CT scanner from GammaMedica was also used to localize the tumor tissues. This Micro-CT scanner uses a microfocal x-ray source (10-220kV, 0.01-0.3 mA). A 2 k×2 k (16 bit) CCD camera is attached to 9'3-field II. The system uses a 7 axis positioning system. For a typical scan, the spatial resolution is 20 microns.

MicroPET studies

Following MRI studies, the mice were transferred to a Concord R4 microPET scanner under anesthesia. The same holder was used for microPET studies so that the tumor positions of the mice remain unchanged in order to facilitate image coregistration with MRI. Subsequently, dynamic microPET scans were performed over 60 min in a list mode, immediately after a bolus injection of ca. 500 µCi of [$^{11}$C]MX via the tail vein. Body temperature in the anesthetized animals was monitored using a rectal temperature probe and maintained at 37+/−2° C. with a heating lamp or a heating pad.

Quantitative Image Analysis

Following MRI and microPET studies, we conducted quantitative image analysis in order to evaluate the in vivo pharmacokinetic profiles of [$^{11}$C]MX in tumor tissues. We defined the tumor tissues as the region of interest (ROI) through coregistration of microPET images with MRI images. The co-registered images were used for quantitative image analysis to determine [$^{11}$C]MX uptake and retention associated with tumor tissues. The radioactivity concentration in the tumor regions is expressed in terms of standard uptake volume (SUV) [(µCi/cc)/(uCi/g)] as a function of time.

Bioassay of AP Sites Following TMZ Treatment

In parallel to the imaging studies, mice of the same batch were also treated with TMZ using the same dose. At 4 hours or 24 hours following TMZ treatment, i.e., the same time points as used in the imaging studies, the tumor tissues were harvested and the AP sites were measured using ARP (aldehyde reactive probe) reagent. The assay was performed as previously described with minor modifications. Briefly, athymic mice carrying human melanoma xenograft were treated intraperitoneally with TMZ (80 mg/kg). Tumors were collected at 4 hours and 1 day after treatment and time-dependent AP sites were measured. After extracting by phenol (Fischer Scientific, Fair Lawn, N.J.) and chloroform (Sigma-Aldrich, St Louis, Mo.), DNA (10 µg) was incubated with 15 µl of 1 mM ARP (Dojindo Laboratories, Kumamoto, Japan) in 150 µl PBS solution at 37° C. for 15 min. DNA was then precipitated with 400 µl ice-cold ethanol (100%) at −20° C. for 20 min and washed with 70% ethanol. DNA was dried at room temperature for 30 min and then resuspended in TE buffer to achieve a final concentration of 0.3 µg/100 µl. The ARP-labeled DNA was then heat-denatured at 100° C. for 5 min, quickly chilled on ice and mixed with an equal amount of 2 M ammonium acetate. The DNA was then immobilized on BA-S 85 nitrocellulose membrane (Schleicher and Schuell, Dassel, Germany) using a minifold II vacuum filter device (Schleicher and Schuell, Dassel, Germany). The membrane was baked at 80° C. for 1 hr and incubated with 0.25% BSA/PBS containing streptavidin-conjugated horseradish peroxidase (BioGenex, SanRamon, Calif.) at room temperature for 40 min with gentle shaking. ARP-labeled AP sites were visualized by chemiluminescence (Amersham Corp, Piscataway, N.J.) followed by quantitative densitometry using NIH ImageJ software.

In Vivo Studies in Melanoma Xenografts

Because TMZ, like dacarbazine, has been used in the treatment patients with metastatic malignant melanoma, we first conducted microPET studies in human (WM164) melanoma xenograft tumor model. In each experiment, two mice bearing melanoma xenografts were used, one treated with TMZ (80 mg/kg) to induce DNA damage and the other used as negative control. Prior to microPET scans, the mice were placed in a 7T MRI scanner and T2-weighted MRI images were acquired following the above-mentioned protocol. While kept in the same position under anesthesia, the mice were then transferred to the microPET scanner. Ten minutes after TMZ treatment, [$^{11}$C]MX (ca. 2 mCi/kg) was then administered through tail vein injection, which was immediately followed by microPET scans for 60 min. The images from MRI scans are shown in FIG. 1A-B. The composite images from microPET scans are shown in FIG. 2C-D. The co-registered images are shown in FIG. 1E-F.

Following microPET and MRI scans, images from both modalities were co-registered for quantificative measurements of [$^{11}$C]MX concentration in each tumor region. As shown in FIG. 2, [$^{11}$C]MX readily entered the tumor tissue at early time points. In the mice treated with TMZ, tumor tissues showed an increased uptake of [$^{11}$C]MX compared to tumor tissues in non-TMZ treated mice. At 10 min post injection of [$^{11}$C]MX, for example, the radioactivity concentration in the TMZ-treated mice was 1.6-fold higher than that in the non-treated mice.

In vivo Studies in Flank Glioma Xenograft

Malignant glioma is another type of cancer that can be effectively treated with TMZ because TMZ can readily penetrate the blood-brain barrier. We thus conducted imaging studies in nude mice of glioma xenografts following a similar protocol as described in the above-mentioned imaging studies. Thus, two mice of glioma xenografts were used in each experiment, one treated with TMZ (80 mg/kg) and the other used as negative control. Prior to microPET studies, the mice were placed in 7T MRI scanner to acquire T2 weighted high resolution MRI image. While kept in the same position under anesthesia, the mice were then transferred to microPET scanner. Ten minutes after TMZ treatment in mice, [$^{11}$C]MX was then administered to both treated and non-treated mice, which was followed immediately by 60 min of microPET scan.

Following image coregistration and quantitative analysis, the radioactivity concentrations of [$^{11}$C]MX were calculated (decay corrected) and plotted as a function of time. As shown in FIG. 3, the retention of [$^{11}$C]MX was higher in TMZ-treated tumor regions than in non-treated tumor regions, suggesting that AP-site formation is elevated following TMZ treatment.

In Vivo Blocking Experiment

Figure 4:
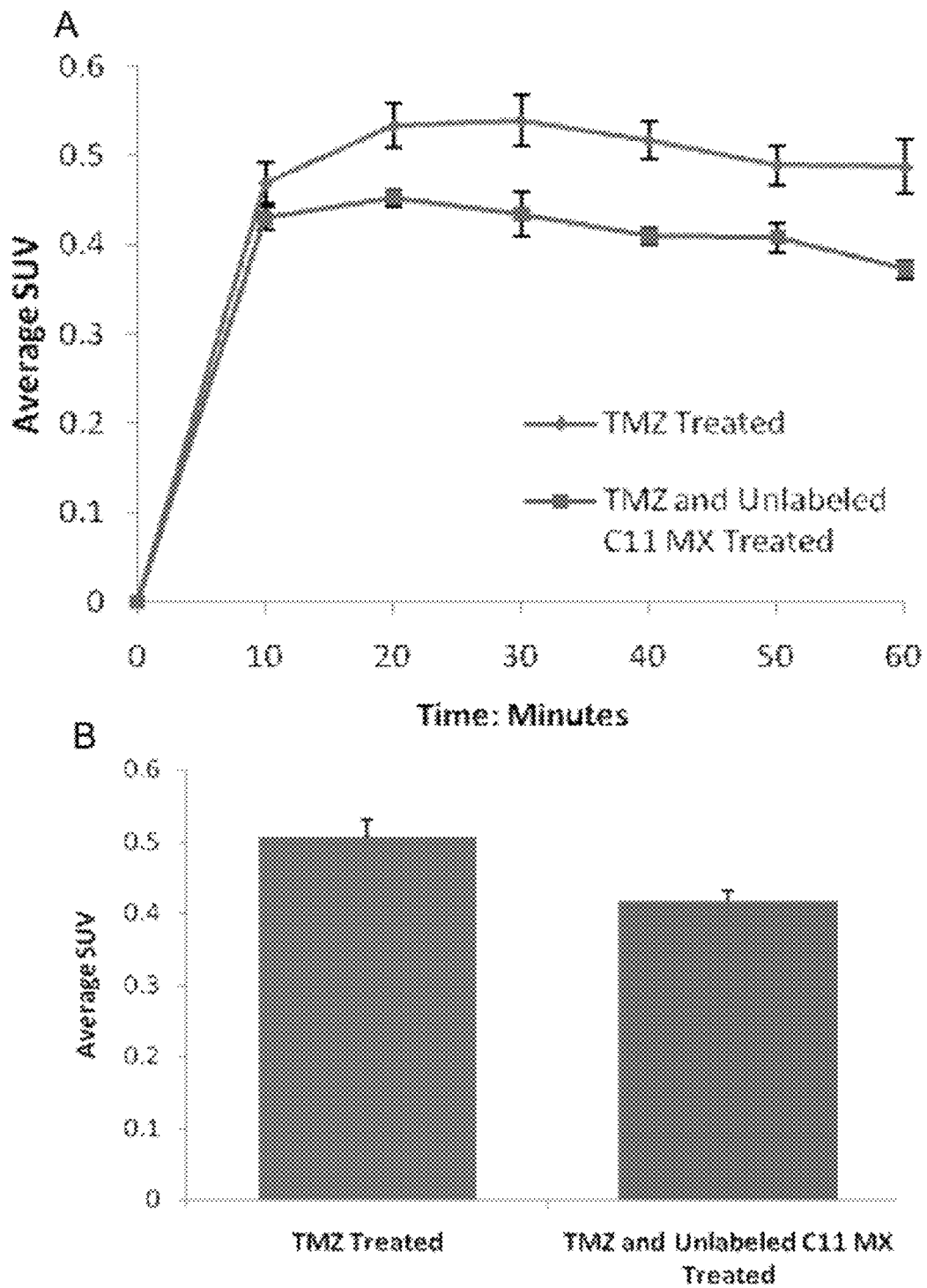
FIG. 4 illustrates; (A) plots of time-radioactivity courses of [$^{11}$C]MX in the glioma tumors before and after blocking by unlabelled MX; and (B) a graph showing average SUV between 0-60 min (n=4, where n is the number of tumors imaged and analyzed). Decrease of radioactivity concentration indicates in vivo blocking of AP binding sites by unlabeled MX (p value=0.003).

For quantitative imaging studies, it is important to demonstrate whether the measured signal is specific for binding of [$^{11}$C]MX to AP sites. Thus, we conducted in vivo blocking experiment in tumor mice with unlabelled MX as a further test of whether the difference in radioactivity concentrations between TMZ-treated and untreated tumors is due to specific binding of [$^{11}$C]MX to AP sites. For this purpose, 4 tumor-bearing mice were treated with TMZ (80 mg/kg) for 10 min. Following the treatment, two mice were injected with unlabelled MX (2-10 mg/kg) and two were injected with vehicle control. Thirty minutes later, 2 mCi/kg of [$^{11}$C]MX was administered to each mouse and microPET imaging was performed. In each case, a vehicle-treated and an unlabeled MX-treated mouse were imaged side-by-side. Dynamic acquisition was carried out for 60 min in list mode. As shown in FIG. 4, the concentration of tumor-associated radioactivity in TMZ-treated mice significantly decreased following treatment with unlabelled MX. This study suggested that the increased retention of radioactivity in the tumor regions was due to specific binding of [$^{11}$C]MX to AP sites.

Figure 5:
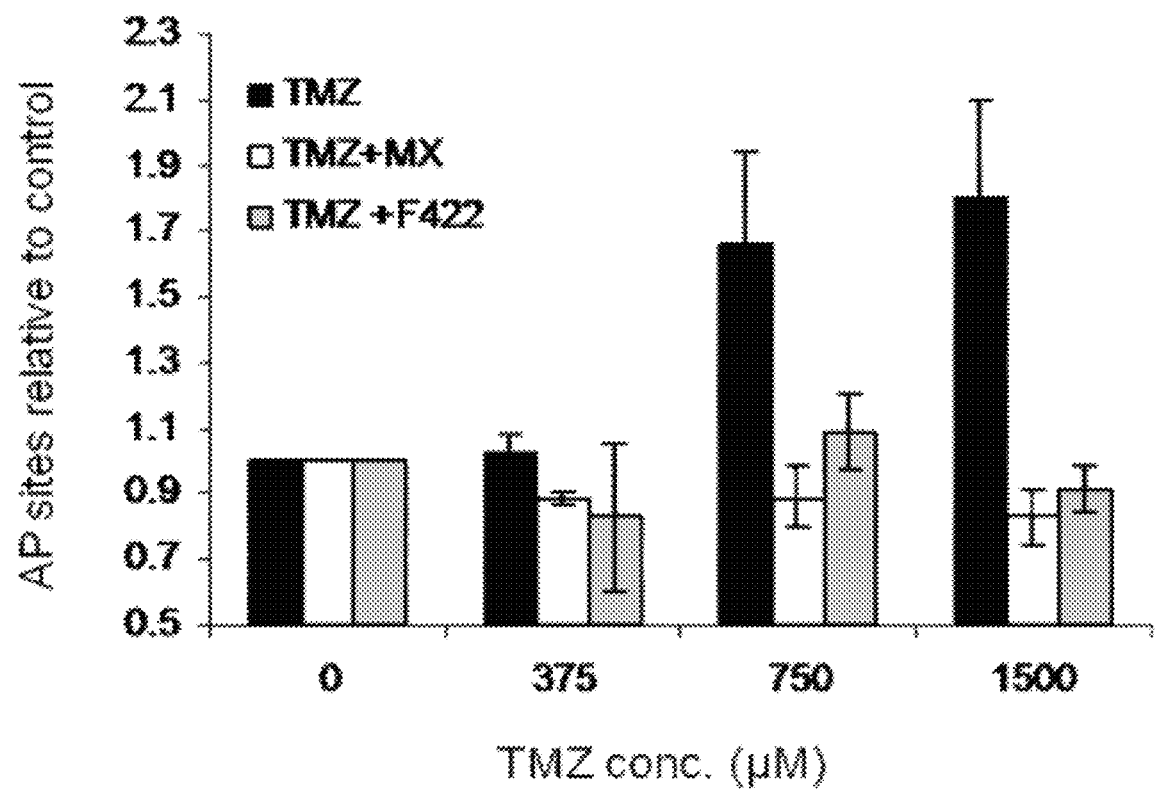
FIG. 5 illustrates a graph showing AP sites increased in melanoma cells (A375) after treatment with TMZ in a dose-dependent manner. Using ARP assay, formation of AP sites in A375 melanoma cells were measured. Cells were treated with TMZ (0-1500 $\mu$M) alone or TMZ plus MX (12.5 mM) for 24 hr for a dose-dependent assay (black), or treated with TMZ and MX (12.5 mM) for 24 hr, or treated with TMZ and F422 (12.5 mM) for 24 hours. Co-treatment with MX or F422 reduced the ARP detected AP sites, suggesting that F422, same as MX, competed with ARP in binding to AP sites induced by TMZ.

To further approve that [$^{11}$C]MX binds specifically to AP sites, we conducted another in vivo binding competition assay using an AP site binding agent, termed F422, which is structurally unrelated to MX. Our preliminary studies have shown that F422 binds potently to AP sites similar to MX (FIG. 5). Thus, the same xenografts bearing melanoma tumors were treated with TMZ (80 mg/kg) for 10 min. Following the treatment, one mouse was injected with unlabelled F422 (10 mg/kg) and the other was injected with vehicle control. Thirty minutes later, 2 mCi/kg of [$^{11}$C]MX was administered to each mouse. MicroPET imaging was then conducted with a vehicle-treated and unlabeled F422-treated mouse side-by-side. Dynamic acquisition was carried out for 60 min in list mode. As shown in FIG. 6, the concentration of tumor-associated radioactivity in TMZ-treated mice significantly decreased following treatment with unlabelled F422. This study further demonstrated that the increased retention of radioactivity in the tumor regions was due to specific binding of [$^{11}$C]MX to AP sites.

Figure 7E:
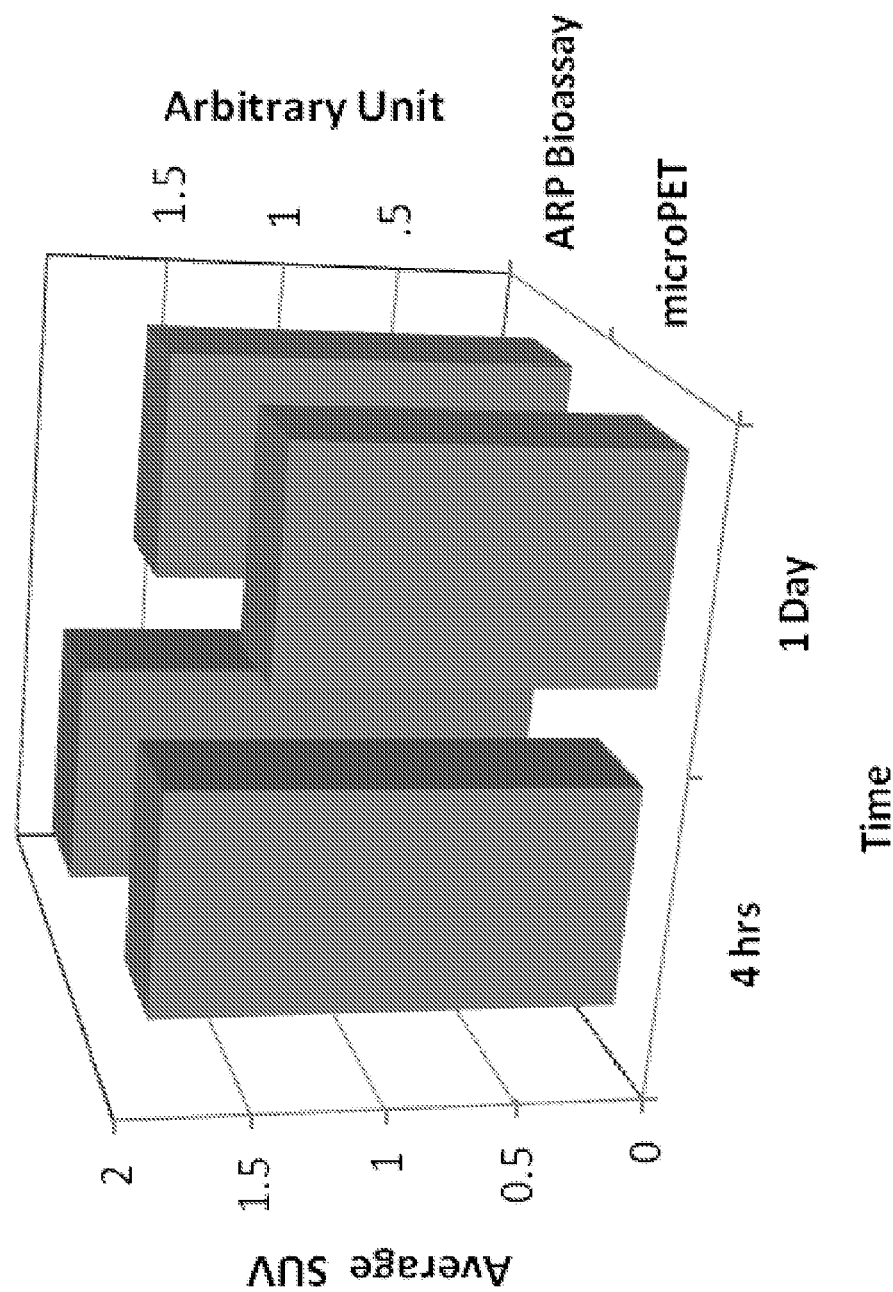
FIG. 7 illustrates the quantification of AP sites at different time points following TMZ treatment in a xenograft tumor mouse model. [$^{11}$C]MX (2 mCi/kg) was injected i.v. to mice anaesthetized with 1.5-2.0% isoflurane and a 60 min PET scan was performed. (A) illustrates a representative CT scan showing the tumor regions; (B) illustrates a representative microPET scan showing the whole-body radioactivity uptake; (C) illustrates fused PET/CT images for quantification of [$^{11}$C]MX uptake; (D) illustrates a plot showing kinetics of [$^{11}$C]MX uptake as a function of time at 4 hours and 1 day after TMZ treatment, with p value=0.001; (E) illustrates averages of radioactivity concentration in the tumor regions over the 60 min scan and correlation with those determined by ARP-based biochemical assays following 4 hours and 1 day treatments of TMZ.
Figure 8:
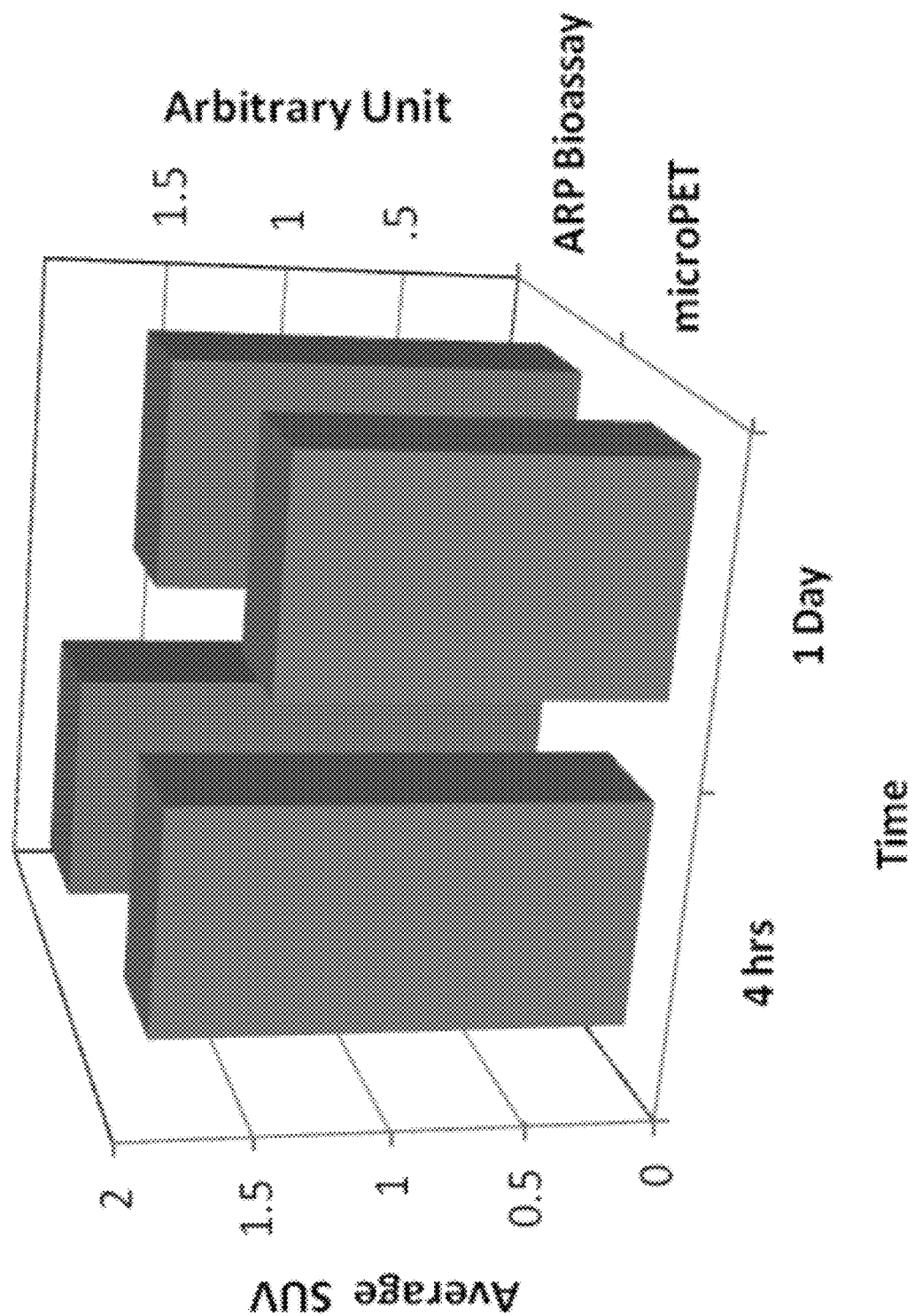

Correlation of Time Course of AP Formation Between In Vivo microPET Studies and In Vitro ARP-Based Biochemical Assays To validate the imaging results, we determined the time course of AP site formation and correlated the in vivo microPET studies with the in vitro ARP-based biochemical assays at different time point. Thus, each group containing a total of three tumor mouse xenografts was subject to TMZ treatment using the same dose (80 mg/kg). One was used for longitudinal imaging at 4 hours and 24 hours and the other two were sacrificed at 4 hours or 24 hours post TMZ treatment for ARP assays. [$^{11}$C]MX uptake as determined by microPET studies was found to be proportional to the amount of AP sites as determined by ARP-based biochemical assays in the tumor tissues that were harvested following TMZ treatment. As shown in FIG. 7, levels of AP-site formation in xenograft tumor tissues were determined separately at 4 hours and 24 hours after mice received a single injection of TMZ (80 mg/kg). Both microPET studies and biochemical assays showed that the levels of TMZ-induced AP sites in tumor tissue were consistently higher at 4 hours than that at 24 hours after TMZ treatment. The same ratios of AP sites between 4 hours and 24 hours were observed in the microPET studies and ARP assays. These studies suggested that [$^{11}$C]MX-PET can be used as an imaging marker of AP formation.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, the following is claimed:

1. A method of measuring the efficacy of an anticancer agent in generating abasic (AP) sites in DNA of cancer cells of a subject, the method comprising:
    administering to the subject an anticancer agent that generates AP sites in at least one cancer cell;
    administering an AP endonuclease inhibitor probe to the subject, the AP endonuclease inhibitor probe including a detection moiety for detecting the probe in the subject,
    measuring the amount of probe bound to cancer cells of the subject, the amount of probe bound to cancer cells of the subject being indicative of efficacy of the anticancer agent in generating AP sites in cancer cells of the subject.

2. The method of claim 1, wherein the AP endonuclease inhibitor probe reacts with an aldehyde of the AP site preventing AP endonuclease cleavage of phosphodiester bonds of the AP site.

3. The method of claim 1, wherein the AP endonuclease inhibitor probe reacts with an aldehyde of the AP site at a rate faster than AP endonuclease cleaves phosphodiester bonds of the AP site.

4. The method of claim 1, the AP endonuclease inhibitor probe comprising at least one of an amine, an amineoxy, a hydrazone, a hydrazine, or a hydroxylamine.

5. The method of claim 1, the detection moiety comprising a radiolabel.

6. The method of claim 5, wherein the AP endonuclease inhibitor probe comprises methoxyamine in which the carbon of the methyl group is substituted with $^{11}$C, at least one hydrogen of the methyl group is substituted with $^{18}$F, the nitrogen is substituted with $^{13}$N, or the oxygen is substituted with $^{15}$O.

7. The method of claim 1, wherein the AP endonuclease inhibitor probe is detected by at least one imaging modality selected from the group consisting of gamma imaging, positron emission tomography (PET) imaging, computer tomography (CT) imaging, magnetic resonance imaging, near infrared imaging, or fluorescent imaging.

8. The method of claim 1, the anticancer agent comprising at least one of an intercalating agent, radiation, a DNA oxidizing agent, an alkylating agent, a radiosensitizing agent, or a cross-linking agent.

9. A method of detecting AP site formation in cancer cells of a subject, comprising
    administering to the subject an anticancer agent that generates AP sites in at least one cancer cell;
    administering an AP endonuclease inhibitor probe to the subject, the AP endonuclease inhibitor probe including a detection moiety for detecting the probe in the subject,
    measuring the amount of probe bound to cancer cells of the subject, the amount of probe bound to cancer cells of the subject being indicative of the amount of AP sites generated in the cancer cells of the subject by the anticancer agent.

10. The method of claim 9, wherein the AP endonuclease inhibitor probe reacts with an aldehyde of the AP site preventing AP endonuclease cleavage of phosphodiester bonds of the AP site.

11. The method of claim 9, wherein the AP endonuclease inhibitor probe reacts with an aldehyde of the AP site at a rate faster than AP endonuclease cleaves phosphodiester bonds of the AP site.

12. The method of claim 9, the AP endonuclease inhibitor probe comprising at least one of an amine, an amineoxy, a hydrazone, a hydrazine, or a hydroxylamine.

13. The method of claim 9, the detection moiety comprising a radiolabel.

14. The method of claim 13, wherein the AP endonuclease inhibitor probe comprises methoxyamine in which the carbon of the methyl group is substituted with $^{11}$C, at least one hydrogen of the methyl group is substituted with $^{18}$F, the nitrogen is substituted with $^{13}$N, or the oxygen is substituted with $^{15}$O.

15. The method of claim 9, wherein the AP endonuclease inhibitor probe is detected by at least one imaging modality selected from the group consisting of gamma imaging, positron emission tomography (PET) imaging, computer tomography (CT) imaging, magnetic resonance imaging, near infrared imaging, or fluorescent imaging.

16. A method of quantifying AP site formation in cancer cells of a subject, comprising:
    administering to the subject an anticancer agent that generates AP sites in at least one cancer cell;
    administering an AP endonuclease inhibitor probe to the subject, the AP endonuclease inhibitor probe including a detection moiety for detecting the probe in the subject,
    measuring the amount of probe bound to cancer cells of the subject by imaging the subject, the amount of probe bound to cancer cells of the subject being indicative of the number of AP sites generated in cancer cells of the subject by the anticancer agent.

17. The method of claim 16, wherein the AP endonuclease inhibitor probe reacts with an aldehyde of the AP site preventing AP endonuclease cleavage of phosphodiester bonds of the AP site.

18. The method of claim 16, the AP endonuclease inhibitor probe comprising at least one of an amine, an amineoxy, a hydrazone, a hydrazine, or a hydroxylamine.

19. The method of claim 16, the detection moiety comprising a radiolabel and the amount AP endonuclease inhibitor probe being measured by positron emission tomography imaging.

20. The method of claim 19, wherein the AP endonuclease inhibitor probe comprises methoxyamine in which a carbon of the methyl group is substituted with 11C or a hydrogen of the methyl group is substituted with 18F.

* * * * *